United States Patent
McTavish

(10) Patent No.: US 10,245,314 B2
(45) Date of Patent: Apr. 2, 2019

(54) NON-SPECIFIC DELAYED-TYPE HYPERSENSITIVITY RESPONSE TO TREAT HERPES SIMPLEX VIRUS INFECTION

(71) Applicant: Squarex, LLC, Pine Springs, MN (US)

(72) Inventor: Hugh McTavish, Pine Springs, MN (US)

(73) Assignee: Squarex, LLC, Pine Springs, MN (US)

( * ) Notice: Subject to any disclaimer, the term of this patent is extended or adjusted under 35 U.S.C. 154(b) by 0 days.

(21) Appl. No.: 15/681,393

(22) Filed: Aug. 20, 2017

(65) Prior Publication Data

US 2017/0340731 A1 Nov. 30, 2017

Related U.S. Application Data

(63) Continuation of application No. PCT/US2016/019978, filed on Feb. 26, 2016.

(60) Provisional application No. 62/120,973, filed on Feb. 26, 2015.

(51) Int. Cl.
| | |
|---|---|
| *A61K 31/04* | (2006.01) |
| *A61K 39/245* | (2006.01) |
| *A61K 39/165* | (2006.01) |
| *A61K 39/12* | (2006.01) |
| *A61K 35/763* | (2015.01) |
| *C07K 14/035* | (2006.01) |
| *G01N 33/571* | (2006.01) |
| *A61K 39/00* | (2006.01) |

(52) U.S. Cl.
CPC .......... *A61K 39/245* (2013.01); *A61K 31/04* (2013.01); *A61K 35/763* (2013.01); *A61K 39/12* (2013.01); *A61K 39/165* (2013.01); *C07K 14/035* (2013.01); *G01N 33/571* (2013.01); *A61K 2039/54* (2013.01); *A61K 2039/545* (2013.01); *A61K 2039/55511* (2013.01); *C12N 2710/16611* (2013.01)

(58) Field of Classification Search
None
See application file for complete search history.

(56) References Cited

U.S. PATENT DOCUMENTS

| | | |
|---|---|---|
| 4,214,592 A | 7/1980 | Jacquet |
| 5,846,559 A | 12/1998 | Hopp |
| 5,965,354 A | 10/1999 | Burke |
| 6,375,952 B1 | 4/2002 | Koelle et al. |
| 6,562,802 B2 | 5/2003 | Johansson et al. |
| 6,692,752 B1 | 2/2004 | Slaoui |
| 6,761,900 B2 | 7/2004 | Shudo et al. |
| 7,037,509 B2 | 5/2006 | Koelle |
| 9,205,065 B2 | 12/2015 | McTavish et al. |
| 2002/0055517 A1 | 5/2002 | Smith |
| 2002/0094337 A1 | 7/2002 | Aurelian et al. |
| 2002/0142005 A1 | 10/2002 | Horn |
| 2004/0076646 A1 | 4/2004 | Caplan |
| 2006/0062762 A1 | 3/2006 | Woodward |
| 2010/0055132 A1 | 3/2010 | Horn et al. |

FOREIGN PATENT DOCUMENTS

| | | |
|---|---|---|
| WO | WO 00/37067 | 6/2000 |
| WO | WO 02/072081 A1 | 9/2002 |

OTHER PUBLICATIONS

Buckley, D.A. et al. 2001, The therapeutic use of topical contact sensitizers in benign dermatoses. *Br. J. Dermatology* 145:385-405.
Kurokowa et al. The Journal of Pharmacology and Experimental Therapeutics, 1999, vol. 289, No. 1, p. 72-78.
Lee et al. Journal of the American Academy of Dermatology, 1999, vol. 41, pp. 595-599.
Roberts et al. 1993. Clinical Psychology Review 13:375-391.
Cardinali et al. 2004. Acta Derm Vereol 84:223-226.
Jarisch et al. (Arch Derm Res 258:151-159, 1977), English abstract only.
Horn TD et al. 2005, Intralesional immunotherapy of warts with mumps, Candida, and Trichophyton skin test antigens: a single-blinded, randomized, and controlled trial. Arch Dermatol. 141(5):589-94.
Liu et al. 2000, CD8(+) T cells can blook herpes simlex vurus type 1 (HSV1) reactivation from latency in sensory neurons. J. Exp. Med. 191:1459-66.

*Primary Examiner* — Stacy B Chen
(74) *Attorney, Agent, or Firm* — Hugh McTavish

(57) ABSTRACT

A method is presented for treating herpes simplex virus (HSV) infection comprising: (a) locally administering a substance that induces a delayed type hypersensitivity (DTH) response to a patient at a site of an HSV lesion to induce a DTH response at the site of the lesion during one or more outbreaks of the HSV infection.

12 Claims, No Drawings

NON-SPECIFIC DELAYED-TYPE HYPERSENSITIVITY RESPONSE TO TREAT HERPES SIMPLEX VIRUS INFECTION

BACKGROUND

Herpes simplex virus (HSV) causes painful lesions on the skin or mucous membranes characterized by vesicles filled with a clear fluid. HSV type 1 (HSV-1) commonly infects the mouth, face, and eyes. HSV type 2 commonly infects the genitals and buttocks. But each serotype can cause infection in all these locations. (Stalkup J R et al., Chapter 80, Human Herpesviruses in *Dermatology*, Bolognia J L et al. eds. 2003, Mosby Edingurgh, United Kingdom).

Primary infection with HSV typically causes mild fever and lesions at the site of infection. Healing occurs in 8-12 days on average, whereupon the virus migrates to nerve ganglia, where it resides in a latent phase. The virus can be activated again by multiple causes, including physical or emotional stress, colds, fever, immune suppression, or no apparent cause. Activation results in secondary outbreaks. For HSV-1, this usually involves cold sores on the vermillion border of the lips. For HSV-2, the secondary outbreak most commonly causes lesions in or around the genitals, including the vulva, vagina, or penis.

Itching, tingling, and a burning sensation usually precede localized erythema of the skin or mucous membranes by a few hours. Vesicles then form on the skin or mucous membranes. After a few days the ulcers dry and become crusted and generally heal in about 10 days.

The outbreaks cause local pain and a mild generalized fever in many cases.

HSV-2 is generally transmitted by sexual contact. HSV-1 is thought to be transmitted by contact with saliva containing the virus. Infection with one or both serotypes of HSV is extremely common. Some have estimated that 90% of the world's population have antibodies to HSV-1. Forty to sixty million persons in the U.S. are infected with HSV-2. (Stalkup J R et al., Supra.)

There is no cure for HSV infection. Antiviral therapy marginally reduces viral shedding and symptoms in secondary outbreaks. Antiviral therapeutics can heal chronic infection in immunocompromised patients. Antiviral therapeutics are also used prophylactically. But antivirals do not cure the infection, and prophylactic antiviral therapy therefore may be needed for a patient's entire life. (Chakrabarty A et al. 2005, *Skin Therapy Lett.* 10(1):1-4.) Even with prophylactic use of antivirals, outbreaks still typically occur, although at a lower frequency. Commonly used antivirals for HSV include acyclovir and its derivatives, e.g., valacyclovir and famciclovir. They are usually given orally, but can also be administered by i.v. or in a topical cream. Docosanol cream (ABREVA) has also been shown to decrease the duration of outbreaks slightly (Sacks S L et al. 2001, *J Am Acad Dermatol.* 45(2):222-30).

New substances and methods to treat HSV infection are needed.

SUMMARY

One embodiment of the invention involves administering a substance that induces a delayed-type hypersensitivity (DTH) reaction locally at a site of an HSV lesion during an outbreak. This causes T cells to swarm the area of the lesion, which has a high concentration of virus. This appears to train the immune system to recognize the herpes simplex virus and strengthens the immune response to the virus, which lessens the severity and frequency of subsequent HSV outbreaks (e.g., cold sores or genital outbreaks) after the treated outbreak or outbreaks. Any compound or mixture that induces a DTH response can be used, including squaric acid dibutyl ester (SADBE), diphenylcyclopropenone (DPCP), 1-chloro-2,4-dinitrobenzene (DNCB), and extract of poison ivy leaves. Protein antigens that induce a DTH response, such as mumps antigen or other antigens a patient might have immunity against, can also be injected into the skin or mucous membrane at the site of an outbreak. The invention has been tested with cold sores, which are caused by herpes simplex virus type 1. It also works with genital herpes, caused by herpes simplex virus type 2.

One embodiment of the invention involves a method of treating herpes simplex virus (HSV) infection comprising: locally administering a substance that induces a delayed type hypersensitivity (DTH) response to a patient at a site of an HSV lesion to induce a DTH response at the site of the lesion during one or more outbreaks of the HSV infection.

Another embodiment of the invention provides a medical use of a substance capable of inducing a delayed-type hypersensitivity response in humans to prepare a medicament effective to reduce the frequency or severity of subsequent HSV outbreaks in a patient with HSV infection.

It has now very surprisingly been found in a clinical trial (described in Example 2 below) with persons that suffer frequent cold sores, herpes labialis lesions on the lip, that topically applying on the inner aspect of the upper arm a substance that induces a DTH response, squaric acid dibutyl ester (SADBE) actually prevented future HSV outbreaks. Patients had topical application of SADBE just once on the upper arm without further application at the site of an HSV lesion, and this actually prevented future outbreaks. The result was statistically significant versus a placebo control group.

This means we can prevent future HSV outbreaks by administering a substance that induces a DTH response at a site other than the site of an HSV outbreak.

The substances that can induce a DTH response are generally in two classes: (1) topical immunosensitizers, such as SADBE, that when applied topically, for instance in a solution in DMSO, induce a DTH response; and (2) recall antigens, such as Candida extract or mumps antigen, that when injected intradermally induce a DTH response.

Thus, one other embodiment provides a method of treating herpes simple virus (HSV) infection comprising: an administering step comprising: (a) applying a topical immunosensitizer to the skin of a person infected with HSV at a site other than the genitals or lips, or to the genitals or the lips but at a time when the person is not having an HSV outbreak on the genitals or lips; or (b) intradermally injecting a recall antigen into a person infected with HSV at a site other than the genitals or lips, or into the genitals or the lips but at a time when the person is not having an outbreak on the genitals or lips; wherein the method does not further comprise (i) applying a topical immunosensitizer to the skin of a person infected with HSV on an HSV lesion at a time of an HSV outbreak in the person; or (ii) intradermally injecting a recall antigen into a person infected with HSV in an HSV lesion at the time of an HSV outbreak in the person.

Another embodiment provides a method of treating herpes simple virus (HSV) infection comprising: an administering step comprising: (a) applying a topical immunosensitizer to the skin of a person infected with HSV at a time when the person is not having an HSV outbreak, or applying a topical immunosensitizer to the skin of a person infected with HSV during an HSV outbreak wherein the applying is at a site other than a site of an HSV lesion; or (b) intradermally injecting a recall antigen into a person infected with HSV at a time when the person is not having an HSV outbreak, or intradermally injecting a recall antigen into a person infected with HSV at a site other than a site of an HSV lesion during an HSV outbreak; wherein the method does not further comprise (i) applying a topical immunosensitizer to the skin of a person infected with HSV on an HSV lesion at a time of an HSV outbreak in the person; or (ii) intradermally injecting a recall antigen into a person infected with HSV in an HSV lesion at the time of an HSV outbreak in the person.

Another embodiment provides a method of treating HSV infection comprising: a first administering step comprising: (a) applying a topical immunosensitizer to the skin of a person infected with HSV at a site other than the genitals or lips, or to the genitals or the lips but at a time when the person is not having an HSV outbreak on the genitals or lips; or (b) intradermally injecting a recall antigen into a person infected with HSV at a site other than the genitals or lips, or into the genitals or the lips but at a time when the person is not having an HSV outbreak on the genitals or lips; and a second administering step comprising: repeating step (a) or step (b) by applying the same topical immunosensitizer or intradermally injecting the same recall antigen on the person at least one other time at a time between 1 week and 2 years after the first administering step.

Another embodiment provides a method of treating herpes simple virus (HSV) infection comprising: an administering step comprising: (a) applying a topical immunosensitizer to the skin on the inner aspect of the upper arm of a person infected with HSV; or (b) intradermally injecting a recall antigen into the skin on the inner aspect of the upper arm of a person infected with HVS; wherein the method reduces the frequency, severity, or duration of HSV outbreaks in the person after the administering step.

Another embodiment provides a medical use of a substance capable of inducing a delayed-type hypersensitivity (DTH) response in humans (a topical immunosensitizer or a recall antigen) to prepare a medicament effective to reduce the frequency of subsequent herpes simplex virus (HSV) outbreaks in a patient with HSV infection when administered to the skin of a person infected with HSV at a time when the person is not having an HSV outbreak or administered to the skin of a person infected with HSV during an HSV outbreak wherein the administering is at a site other than a site of an HSV lesion.

Another embodiment provides a medical use of a topical contact sensitizer or a recall antigen to prepare a medicament effective to reduce the frequency of subsequent herpes simplex virus (HSV) outbreaks in a patient with HSV infection when administered by (a) applying a topical immunosensitizer to the skin on the inner aspect of the upper arm of a person infected with HSV; or (b) intradermally injecting a recall antigen into the skin on the inner aspect of the upper arm of a person infected with HSV.

Another embodiment provides a method of treating HSV infection comprising a first administering step comprising: (a) applying a topical immunosensitizer to the skin of a person infected with HSV at a site other than the genitals or lips, or to the genitals or the lips but at a time when the person is not having an outbreak on the genitals or lips; and a second administering step comprising (b) applying the same topical immunosensitizer onto an epithelial HSV lesion at the site of the lesion during an HSV outbreak in the person; wherein the second administering step occurs at least 1 week after the first administering step; wherein the second administering step does not produce localized erythema at the site of administration on the person.

Another embodiment provides a composition comprising a topical immunosensitizer or a recall antigen for use in a method of treating HSV infection, the method comprising: an administering step comprising: (a) applying a topical immunosensitizer to the skin of a person infected with HSV at a time when the person is not having an HSV outbreak, or applying a topical immunosensitizer to the skin of a person infected with HSV during an HSV outbreak wherein the applying is at a site other than a site of an HSV lesion; or (b) intradermally injecting a recall antigen into a person infected with HSV at a time when the person is not having an HSV outbreak, or intradermally injecting a recall antigen into a person infected with HSV at a site other than a site of an HSV lesion during an HSV outbreak; wherein the method does not further comprise (i) applying a topical immunosensitizer to the skin of a person infected with HSV on an HSV lesion at a time of an HSV outbreak in the person; or (ii) intradermally injecting a recall antigen into a person infected with HSV in an HSV lesion at the time of an HSV outbreak in the person; wherein the method reduces the frequency of new HSV outbreaks in the person after the administering step.

Another embodiment provides a composition comprising a topical immunosensitizer or a recall antigen for use in a method of treating HSV infection, the method comprising: an administering step comprising: (a) applying a topical immunosensitizer to the skin on the inner aspect of the upper arm of a person infected with HSV; or (b) intradermally injecting a recall antigen into the skin on the inner aspect of the upper arm of a person infected with HSV; wherein the method reduces the frequency of new HSV outbreaks in the person after the administering step.

The methods reduce the frequency, duration, or severity outbreaks in the person after the administering step or steps. The term "applying a topical immunosensitizer to the skin" includes intradermally injecting the topical immunosensitizer, although usually the topical immunosensitizer would be applied topically.

DETAILED DESCRIPTION

One embodiment of the invention involves a method of treating herpes simplex virus (HSV) infection comprising: locally administering a substance that induces a delayed type hypersensitivity (DTH) response to a patient at a site of an HSV lesion to induce a DTH response at the site of the lesion during one or more outbreaks of the HSV infection. An "outbreak" refers to a temporal episode of burning, tingling, painful, or visible lesions arising from HSV infection. Outbreaks are separated by dormant periods when the patient has no symptoms of infection.

A delayed-type hypersensitivity (DTH) response, also known as a type IV hypersensitivity response, is an immune response that typically reaches maximal intensity 24-48 hours after contact with an immunogen. It produces visible erythema at the site of contact with the immunogen. A DTH response is primarily a T cell response (Goldsby, Richard A. et al. 2000, *Kuby Immunology*, 4th edition, WH Freeman and Co., New York, chapter 16). It occurs when antigen activates sensitized $T_{DTH}$ cells. Activation of the $T_{DTH}$ cells results in secretion of several cytokines, which draws macrophages into the area and activates them.

T cells and cell-mediated immunity are the primary arm of the immune system responsible for fighting viral infection. Cell-mediated immunity is responsible for recognizing and eliminating cells that harbor intracellular pathogens, such as HSV. Without wishing to be bound by theory, the inventors believe the DTH response of the present invention causes T cells to swarm the area of an HSV outbreak. With a large number of HSV viral particles and HSV proteins in the area during an outbreak, the T cells better learn to recognize HSV and cells harboring HSV, resulting in a stronger immune response to HSV in the future that does a better job of ridding the body of the virus and viral-infected cells, thus preventing outbreaks and lessening the severity of outbreaks. This is a process of "epitope unveiling" whereby epitopes that were poorly recognized by the immune system become better recognized.

It has previously been shown that warts caused by human papilloma virus can be treated by inducing a DTH response at the site of a wart with topical application of contact sensitizers, such as DNCB, or with intralesional injection of protein antigens unrelated to human papilloma virus that induce a DTH response in the patient, such as mumps antigen, candida antigen, or trichophyton antigen. (U.S. Pat. No. 6,350,451; U.S. published patent application no. 20050175634; Johansson, E. et al. 1984, Dinitrochlorobenzene (DNCB) treatment of viral warts, *Acta Derm. Verereol (Stockh)* 64:529-533; Dunnigan, W. G. et al., 1982, Dinitrochlorobenzene immunotherapy for verrucae resistant to standard treatment modalities, *J. Am. Acad. Dermatol.* 6:40-45.) The present invention appears to work by a similar mechanism.

The immunogen of the present invention used to induce the DTH response can be a protein antigen that the subject has previously encountered and to which he or she has developed immune recognition. This is the principle of skin tests for allergens or antigens such as the tuberculosis antigen. The immunogen can also be a topical contact sensitizer, such as urushiol, an oil that is the active irritating ingredient in poison ivy, poison oak, and other irritating plants. Topical contact sensitizers are typically haptens. Haptens are small molecules that do not induce an immune response on their own, but can induce an immune response and antibodies that specifically recognize the hapten determinant when attached to proteins or other macromolecules. Topical contact sensitizers are typically haptens that react with proteins in the skin to form adducts that are immunogenic.

Thus, in some embodiments the substance that induces a DTH response is a topical contact sensitizer—a substance that when applied topically to human skin induces a DTH response. Topical contact sensitizers are also referred to herein as topical immunosensitizers. The two terms have the same meaning and are used interchangeably.

Thus, in some embodiments the method involves topically applying a substance that induces a DTH response to a patient at a site of an HSV lesion to induce a DTH response at the site of the lesion.

A topically applied contact sensitizer is typically applied as a solution in an organic solvent, e.g., acetone or dimethylsulfoxide. If soluble in water, it can instead by applied in an aqueous solution. It can also be applied in a cream, ointment, lotion, oil, etc.

In specific embodiments where the substance that induces a DTH response is applied topically (is a topical contact sensitizer) the substance is squaric acid dibutyl ester (SADBE), diphenylcyclopropenone (DPCP), 1-chloro-2,4-dinitrobenzene (DNCB), or 1-chloro-2,6-dinitrobenzene. In some embodiments, the substance is squaric acid or an ester thereof. In a more specific embodiment, it is a squaric acid diester, for instance, squaric acid diethyl ester or squaric acid dibutyl ester (SADBE).

The structure of squaric acid is shown below.

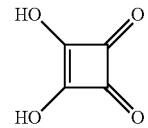

SADBE has the systemic name of 3,4-Dibutoxy-3-cyclobutene-1,2-dione. Its structure is shown below:

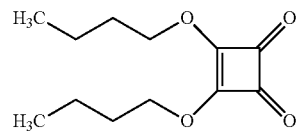 [SMILES: CCCCOc1c(OCCCC)c(=O)c1=O]

These contact sensitizers are available from several commercial sources, including Spectrum Chemicals & Laboratory Products, a division of Spectrum Chemical Manufacturing Corp., Gardena, Calif. and New Brunswick, N.J.

In other embodiments, the substance that induces a DTH response comprises urushiol or an extract of an irritating plant.

The term "topical contact sensitizer" as used herein has the same meaning as "topical immunosensitizer." The two terms mean any substance that when topically applied to human skin induces a localized DTH response (as evidenced by local erythema at the site of administration that peaks in a delayed manner, for instance, at about 2 days after administration, rather than peaking within the first 24 hours of administration) in a majority of previously sensitized persons. An appropriate test is application of a test substance at a concentration of 2% w/v in acetone or DMSO in a volume of 0.2 ml to a skin area of 1 cm squared or less (test application), after prior application of the same substance in the same concentration and amount to the same person (sensitization application) in the period of 2-12 weeks prior to the test application. For a topical contact sensitizer, the test application will induce a localized DTH response in the majority of persons.

In other embodiments, the substance that induces a DTH response is a protein antigen. The protein antigen is typically not an HSV antigen, although it could be. Any antigen that induces a DTH response can be used. A subject may have a preexisting sensitivity to the antigen. Mumps antigen, candida antigen, and trichophyton antigen are three preferred antigens in this regard, since a large percentage of the population has a preexisting sensitivity to one or more of these antigens. Other foreign (non-self) antigen to which a subject does not have a preexisting sensitivity can also be used. In that case, the subject should be sensitized to the antigen by administering the antigen to the subject (i.e., immunizing the subject with the antigen) before locally administering the antigen to the subject at a site of HSV outbreak to induce a DTH response at the site of an outbreak.

In specific embodiments, the substance that induces a DTH response is a recall antigen.

The prototypical recall antigens are those commonly used in immunologic skin testing to test immune response, particularly mumps antigen, candida antigen, and trichophyton antigen. The test shows if the body "remembers" or "recalls" the antigen, i.e., has a delayed-type hypersensitivity response in the skin where the antigen was administered by intradermal injection.

The term "recall antigen" is defined herein as a substance or mixture containing a plurality of proteinaceous antigens, wherein the substance or mixture induces a delayed-type hypersensitivity response (as evidenced by delayed appearance of erythema) in intradermal skin test in a majority of immunocompetent people previously sensitized or exposed to the recall antigen. The prototypical recall antigens are those commonly used in immunologic skin testing to test immune response, particularly mumps antigen, candida antigen, and trichophyton antigen. Each of these, although referred to by the singular term "antigen" is actually composed of several or many molecular substances that can induce an immune response.

In specific embodiments, the recall antigen may be mumps antigen (e.g., killed whole mumps virus), Candida extract, or Trichophyton extract.

In specific embodiments, the recall antigen is killed whole virus, killed whole bacteria, or killed whole microorganisms.

Thus, in some embodiments, the method involves intralesionally (e.g., intradermally) injecting the substance that induces a DTH response into a patient at a site of an HSV lesion in the patient to induce a DTH response at the site of the lesion.

In a specific embodiment of intralesionally injecting the substance, the substance comprises mumps antigen, candida antigen, or trichophyton antigen.

The dosages of antigen can be approximately the same as the dosages used in skin tests with these antigens. The dose should be a dose that induces a mild to moderate DTH response.

In a specific embodiment, the method further comprises before inducing a DTH response at the site of an outbreak, administering the substance that induces a DTH response to the patient to develop a sensitivity to the substance in the patient. This presensitization step can be done with intralesionally injected antigens or with topically applied substances. For the presensitization step, the substance can be administered at the site of outbreak. This may be beneficial to help stimulate recognition of HSV and HSV-infected cells. Or for the presensitization step, the substance can be administered anywhere. For instance, a topical contact sensitizer may be administered on the forearm, or an injectable antigen may be administered by intradermal injection to the forearm, during a time when the patient may or may not be suffering an outbreak.

In a specific embodiment, the method can involve, before the step of inducing a DTH response at the site of an HSV lesion, administering the substance that induces a DTH response to the patient at least one dosage level to determine a dosage level of the substance to administer to induce a DTH response at the site of an HSV lesion.

The lips and genitals, which are the most common areas for lesions of HSV-1 and HSV-2 outbreaks respectively, are both very sensitive areas. The lips are also a very visible area. Thus, it is desirable to not induce a severe DTH response in these sites because such a severe response can be painful and unsightly. Therefore, one may want to test one or more dosages of the substance in a less sensitive and less visible area, such as the forearm, to find a dose that induces an appropriate level of DTH response before applying the substance at the site of an HSV lesion. It has been found that the method works even when the DTH response at the site of an HSV lesion is fairly mild. It does not appear to be necessary to induce a severe DTH response. But the methods may be more effective in inducing a sustained immunity to HSV that prevents subsequent outbreaks if the DTH response is stronger.

It is not essential to induce a DTH response for the methods to work. In our clinical trial described in Example 2, the treated patients who did not develop a visible erythema at the site of application of SADBE nonetheless had a longer median time to the next HSV outbreak than patients receiving placebo.

Thus, in all methods described herein where the method involves inducing a DTH response, it can involve administering a substance (topical immunosensitizer or recall antigen) capable of inducing a DTH response, without actually inducing a visible DTH response. This is true whether the administering is at the site of an HSV lesion or elsewhere on the person's body.

For DNCB, a suitable sensitizing dose appears to be a 2% DNCB solution in acetone, dimethylsulfoxide (DMSO), or another solvent, and a suitable treatment dose is, for example, 0.05 to 2.0% DNCB. A suitable sensitizing dose of SADBE is a 2% solution, and a suitable treatment dose is, for example, a 0.05%-2% solution. Doses that are higher or lower than these ranges can also be used in some patients.

The topical contact sensitizer solution in one embodiment is applied by dabbing a cotton-tipped swab that has been saturated with the solution onto the skin or mucous membrane at the desired site of application, without repeated rubbing or spreading the solution over an extended area. For both the sensitization and treatment applications, the topical contact sensitizer is preferably left on the skin for at least a few hours before washing it off.

In another embodiment, the contact sensitizer solution is applied with a fixed volume device, such as a micropipette, syringe, or microsyringe. This allows application of a defined volume and therefore a defined amount of the contact sensitizer. That can be helpful to produce a more predictable level of intensity of the DTH response. A typical volume is 2-40 microliters to be able to apply the solution to a targeted and limited area such as a lesion without the solution spreading or running to nontarget areas.

In particular embodiments of the methods, the herpes simplex virus is HSV type 1. In other embodiments, it is HSV type 2.

In particular embodiments, the method involves administering the substance that induces a DTH response at the site of an HSV lesion on or adjacent to the lip of the patient.

In particular embodiments, the method involves administering the substance that induces a DTH response at the site of an HSV lesion on the genitals of the patient.

In particular embodiments, the method involves topically applying the substance that induces a DTH response to skin at a site of an HSV lesion. In other embodiments, it involves topically applying the substance to a mucous membrane at a site of an HSV lesion.

The method can reduce the severity of future outbreaks or the frequency of future outbreaks, or both. The method is not intended to reduce the severity of the outbreak during which the DTH response is elicited at the site of an HSV lesion. In fact, it may actually worsen that particular outbreak. The DTH response involves inflammation and can produce a mild fever. Inflammation and fever are themselves triggers for HSV outbreaks, so the DTH response may trigger the HSV to worsen its current outbreak. But once that outbreak subsides or is brought under control, subsequent outbreaks are found to be much less frequent and/or severe.

To counteract the tendency of the DTH response to worsen the HSV outbreak during which the DTH response is induced, in one embodiment, the method can involve treating the patient with antiviral medications, such as acyclovir or valacyclovir, during the outbreak in which the DTH response is induced.

The step of inducing a DTH response at a site of an HSV lesion can be repeated more than once to further strengthen the immune response to HSV, if further outbreaks occur. Preferably, treatments are spaced apart by at least two weeks to allow full development of the immune response from the previous treatment.

Many patients may require more than one treatment to develop a level of immunity that decreases the number or severity of subsequent outbreaks (i.e., outbreaks subsequent to the treatment, outbreaks in which no substance is administered to induce a DTH response). Preferably, the immunity developed completely prevents subsequent outbreaks. Thus, the substance that induces a DTH response is administered to a lesion in one outbreak. When the outbreak subsides and a subsequent recurrent outbreak occurs, the substance may be administered to a lesion again. After administration of the substance during 1 to 3 or more outbreaks, the patient may have no outbreaks for an extended period of time. But the immunity may eventually wear off, and outbreaks may recur. A substance that induces the DTH response can then be applied again during one or more outbreaks as needed to develop immunity again that prevents outbreaks.

Thus, in one embodiment the method comprises: (a) locally administering a substance that induces a delayed type hypersensitivity (DTH) response to a patient at a site of an HSV lesion to induce a DTH response at the site of the lesion during one outbreak of the HSV infection (for example, during only one outbreak over a 6-month period). In one embodiment the method comprises: locally administering a substance that induces a delayed type hypersensitivity (DTH) response to a patient at a site of an HSV lesion to induce a DTH response at the site of the lesion during one outbreak of the HSV infection; wherein the method does not comprise administering a substance that induces a DTH response to the patient at a site of an HSV lesion to induce a DTH response at the site of the lesion during another outbreak within 3 months before or after the one outbreak.

In other embodiments, the method comprises: (a) locally administering a substance that induces a delayed type hypersensitivity (DTH) response to a patient at a site of an HSV lesion to induce a DTH response at the site of the lesion during two or more outbreaks of the HSV infection (for example, during two or more outbreaks in a 6-month period).

One embodiment of the invention provides a medical use of a substance capable of inducing a delayed-type hypersensitivity response in humans to prepare a medicament effective to reduce the frequency or severity of herpes simplex virus (HSV) outbreaks.

In particular embodiments, the substance is a topical contact sensitizer capable of inducing a DTH response in humans when administered topically.

In other embodiments, the substance is an antigen capable of inducing a DTH response in humans when injected intradermally.

By reducing the duration and severity of subsequent outbreaks, the methods of the invention also reduce transmission of infection. This is true for both HSV-1 infection and HSV-2 infection, and of both genital herpes and oral herpes.

In one embodiment of the methods, the method reduces transmission of infection of HSV-1.

In one embodiment of the methods, the method reduces transmission of infection of HSV-2.

In one embodiment of the methods of the invention, the method reduces transmission of oral herpes infection.

In one embodiment of the methods of the invention, the method reduces transmission of genital herpes infection.

In specific embodiments, the methods decrease frequency of subsequent outbreaks by at least 50% (i.e., increase time to next outbreak after treatment by at least 100%). In other embodiments, the methods decrease frequency of subsequent outbreaks by at least 75%. In other embodiments, the methods decrease frequency of subsequent outbreaks by at least 70%, at least 80%, or at least 90%. In one embodiment, the methods increase time between outbreaks. In specific embodiments, the methods increase time between outbreaks (e.g., increase the time from resolution of the outbreak treated to the next subsequent outbreak, as compared to the average time between outbreaks previously) at least 2-fold, at least 3-fold, at least 4-fold, or at least 5-fold.

The immune effects of the steps of administering the topical immunosensitizer or recall antigen are believed to take 2 weeks or more to develop. And inflammation that is characteristic of the DTH response can take up to 3 weeks to fully dissipate. Inflammation is a known trigger for HSV outbreaks, so the reduction in HSV outbreaks after the administering step or steps may not fully take effect until 3 weeks after the administering step. So in specific embodiments, the methods decrease frequency of outbreaks that begin at least 21 days after the administration step. In specific embodiments, the methods increase median time from day 21 following the administering step to the next outbreak that begins at least 21 days after the administration step by at least 2-fold, or by at least 3-fold, or by at least 4-fold.

In specific embodiments, the methods of the invention reduce the duration of subsequent outbreaks. In particular embodiments, they reduce the time to healing of lesions in subsequent outbreaks by at least 10%, at least 20%, at least 30%, or at least 40%.

The methods are believed to stimulate cell-mediated immunity. Cell-mediated immunity may be assayed by peripheral blood mononuclear cell proliferation assays, as described in Example 2 below. In specific embodiments of the methods, the method increases stimulation index of peripheral blood mononuclear cells (as illustrated in Example 2) in a proliferation assay of stimulation by HSV particles. In specific embodiments, it increases the stimulation index from less than 30 before treatment to more than 30, more than 50, or more than 60 after treatment. In other embodiments, it increases the stimulation index from less than 50 before treatment to more than 50 or more than 60 after treatment. In other embodiments, it increases the stimulation index by at least 10, at least 20, at least 30, at least 40, or at least 50. In other embodiments, it at least doubles, at least triples, or at least quadruples the stimulation index.

Immune response enhancers can also be used with the substance that induces a DTH response to enhance development of immunity against HSV with the DTH response. One type of enhancer that can be used is a cytokine. Among the cytokines that may be used are an interferon (e.g., interferon alpha), granulocyte monocyte colony stimulating factor (GM-CSF), interleukin-2, and interleukin-12. Each of these has been shown to promote cell-mediated immune reactions or antiviral immune reactions (Kiline M O et al.

2006, *J. Immunol.* 177:6962-73; Arora A. et al. 2006, *J. Surg. Oncol.* 94:403-412; Horn et al., US Published Patent Appl. No. 20050175634).

U.S. Published Patent Appl. 20050175634 reports intralesional injection of unrelated antigens to induce a DTH response in warts. It reports a study where a portion of the patients received intralesional injection of antigens only, and others received as well intralesional injection of interferon alpha or GM-CSF. A larger fraction of patients receiving interferon or GM-CSF together with the antigens responded to treatment than patients receiving antigen alone, although the number of subjects treated was not enough for the differences to be statistically significant.

Appropriate doses of the cytokines are known in the art or can be determined by experimentation to identify a dosage range that gives best results. A suitable dose of interferon alpha, for example, is approximately 1 million IU administered locally.

Administration of the cytokines may be by intradermal injection at the site of the lesion. It may also be by topical administration, e.g., in an ointment, cream, or lotion (Syed T A et al. 1995. *J. Mol. Medicine* 73:141-144).

In another embodiment, the immune response enhancer is a pharmaceutical agent that stimulates synthesis of cytokines. In one embodiment, it is a synthetic (i.e., not a naturally occurring molecule) pharmaceutical agent that stimulates synthesis of cytokines. Specific examples are imiquimod and resiquimod. (Spruance S L et al. 2001, *J. Infect. Dis.* 184:196-200; Bernstein D I et al. 2005, *Clinical Infectious Disease* 41:808-814.)

The immune response enhancer can be administered at any suitable time that will result in it having an effect during the DTH response. This may be at the same time as the time that the substance that elicits a DTH response is administered or somewhat before or after. It should be administered before or during the DTH response.

With the discovery that application of a topical immunosensitizer to the arm of a patient at a time the patient may or may not be having an HSV outbreak reduces the frequency of future outbreaks, even without ever administering a topical immunosenzitizer or recall antigen at the site of an HSV lesion, another embodiment provides a method of treating herpes simple virus (HSV) infection comprising: an administering step comprising: (a) applying a topical immunosensitizer to the skin of a person infected with HSV at a time when the person is not having an HSV outbreak, or applying a topical immunosensitizer to the skin of a person infected with HSV during an HSV outbreak wherein the applying is at a site other than a site of an HSV lesion; or (b) intradermally injecting a recall antigen into a person infected with HSV at a time when the person is not having an HSV outbreak, or intradermally injecting a recall antigen into a person infected with HSV at a site other than a site of an HSV lesion during an HSV outbreak; wherein the method does not further comprise (i) applying a topical immunosensitizer to the skin of a person infected with HSV on an HSV lesion at a time of an HSV outbreak in the person; or (ii) intradermally injecting a recall antigen into a person infected with HSV in an HSV lesion at the time of an HSV outbreak in the person.

Another embodiment provides a method of treating HSV infection comprising: a first administering step comprising: (a) applying a topical immunosensitizer to the skin of a person infected with HSV at a site other than the genitals or lips, or to the genitals or the lips but at a time when the person is not having an HSV outbreak on the genitals or lips; or (b) intradermally injecting a recall antigen into a person infected with HSV at a site other than the genitals or lips, or into the genitals or the lips but at a time when the person is not having an HSV outbreak on the genitals or lips; and a second administering step comprising: repeating step (a) or step (b) by applying the same topical immunosensitizer or intradermally injecting the same recall antigen on the person at least one other time at a time between 1 week and 2 years after the first administering step.

Another embodiment provides a method of treating herpes simple virus (HSV) infection comprising: an administering step comprising: (a) applying a topical immunosensitizer to the skin on the inner aspect of the upper arm of a person infected with HSV; or (b) intradermally injecting a recall antigen into the skin on the inner aspect of the upper arm of a person infected with HVS; wherein the method reduces the frequency, severity, or duration of HSV outbreaks in the person after the administering step.

The inner aspect of the upper arm refers to the surface of the upper arm that is in contact with the chest when a person holds their arms relaxed at their sides. This is where the initial dose of topical immunosensitizer was applied in the clinical trial described in Example 2, where efficacy was proven. The inner aspect of the upper arm is a favorable spot for application of the substance because the application may cause a rash, and the inner aspect of the upper arm is hidden by clothing, so any rash is not unsightly or embarrassing. It also is near a major lymph node in the armpit, and that may be part of the reason for the efficacy. So it may be the inner aspect of the upper arm is a particularly favorable spot to apply the drug for efficacy purposes, as well as being a hidden spot on the body in case a rash develops.

Again, in specific embodiments of the methods of treating HSV described herein, the method reduces the frequency of new HSV outbreaks in the person after the administering step.

In specific embodiments, the method comprises applying a topical immunosensitizer to the skin of a person infected with HSV at a time when the person is not having an HSV outbreak, or applying a topical immunosensitizer to the skin of a person infected with HSV during an HSV outbreak wherein the applying is at a site other than a site of an HSV lesion.

In specific embodiments, the administering step comprises applying the topical immunosensitizer to skin on the inner aspect of the upper arm of the person or intradermally injecting a recall antigen into skin on the inner aspect of the upper arm of the person.

In specific embodiments, the topical immunosensitizer comprises squaric acid, a squaric acid ester, diphenylcyclopropenone (DPCP), 1-chloro-2,4-dinitrobenzene (DNCB), or 1-chloro-2,6-dinitrobenzene.

In specific embodiments, the topical immunosensitizer is SADBE and is applied as a solution in DMSO.

In specific embodiments, the treated person has herpes labialis.

In specific embodiments, the person has genital herpes.

In specific embodiments, the method decreases time to healing of lesions in a subsequent outbreak of the HSV infection after step (a) by at least 30%.

In specific embodiments, the method increases time between outbreaks by at least 2-fold.

In specific embodiments, the method increases time between outbreaks by at least 4-fold.

In specific embodiments, the method at least doubles stimulation index of peripheral blood mononuclear cells (PBMC) from a patient in a proliferation test with stimulation of proliferation by killed HSV particles as compared to the stimulation index of PBMC from the patient before treatment.

In specific embodiments, the method increases median time to the next outbreak after the administering step by at least 2-fold, at least 3-fold, or at least 4-fold.

In specific embodiments, the method increases median time from day 21 following the administering step to the next outbreak that begins at least 21 days after the administering step by at least 2-fold, at least 3-fold, or at least 4-fold.

Again, one embodiment provides a method of treating herpes simple virus (HSV) infection comprising: a first administering step comprising: (a) applying a topical immunosensitizer to the skin of a person infected with HSV at a time when the person is not having an HSV outbreak, or applying a topical immunosensitizer to the skin of a person infected with HSV during an HSV outbreak wherein the applying is at a site other than a site of an HSV lesion; or (b) intradermally injecting a recall antigen into a person infected with HSV at a time when the person is not having an HSV outbreak, or intradermally injecting a recall antigen into a person infected with HSV at a site other than a site of an HSV lesion during an HSV outbreak; wherein the method does not further comprise (i) applying a topical immunosensitizer to the skin of a person infected with HSV on an HSV lesion at a time of an HSV outbreak in the person; or (ii) intradermally injecting a recall antigen into a person infected with HSV in an HSV lesion at the time of an HSV outbreak in the person.

In specific further embodiments of this, the method further comprises a second administering step comprising: (a) applying a topical immunosensitizer to the skin of a person infected with HSV at a time when the person is not having an HSV outbreak, or applying a topical immunosensitizer to the skin of a person infected with HSV during an HSV outbreak wherein the applying is at a site other than a site of an HSV lesion; or (b) intradermally injecting a recall antigen into a person infected with HSV at a time when the person is not having an HSV outbreak, or intradermally injecting a recall antigen into a person infected with HSV at a site other than a site of an HSV lesion during an HSV outbreak.

In specific embodiments, the second administering step occurs 7 days to 30 days after the first administering step.

In specific embodiments, the second administering step occurs 7 days to 365 days after the first administering step and occurs at a time when the person is having an HSV outbreak (but involves administering at a site other than a site of an HSV lesion during the HSV outbreak).

In specific embodiments, the first and second administering steps both comprise: (a) applying a topical immunosensitizer to the skin of a person infected with HSV at a time when the person is not having an HSV outbreak, or applying a topical immunosensitizer to the skin of a person infected with HSV during an HSV outbreak wherein the applying is at a site other than a site of an HSV lesion.

In specific embodiments, the first or subsequent administering steps in produce an erythema in the person at the site of administering. In other embodiments, the first or subsequent administering steps do not produce an erythema in the person at the site of administration.

In specific embodiments where the topical immunosensitizer or recall antigen are administered at a site other than the site of an HSV lesion, the administering step comprises applying the topical immunosensitizer to skin on the spine of the person or skin over the trigeminal ganglion of the person or intradermally injecting a recall antigen into skin on the spine of the person or skin over the trigeminal ganglion of the person. HSV is known to reside in the spine and in the trigeminal ganglion, so these may be effective sites for administering the topical immunosensitizer or the recall antigen.

The invention will now be illustrated by the following examples. The examples are intended to illustrate the invention but not limit its scope.

EXAMPLES

Example 1

Treatment of an Individual Suffering from Frequent and Severe Cold Sores

The individual treated was one of the inventors. He is a male and was 42 years old at the time of this treatment. The subject suffered from frequent cold sores on the lower lip. The outbreaks typically lasted 7-10 days and frequently longer. The subject had suffered from frequent cold sores most of his life. During the 6 months prior to this treatment, the outbreaks had been almost continuous. After getting over one outbreak, the next outbreak would begin often within a week.

The subject was presensitized to DNCB by dipping a cotton-tipped swab in a 2% DNCB solution in acetone, and contacting the cotton-tipped swab with two spots on the forearm. No rash developed. Two weeks later, the subject again applied a 2% DNCB solution to his forearm at two small spots different from where the sensitizing dose had been applied. A very strong but localized rash ensued and lasted for 3 weeks. The subject then applied a 0.1%, 0.2%, and 0.3% solutions to separate small spots on the forearm. The 0.1% solution produced almost no erythema. The 0.2% solution produced a mild but easily seen erythema that began 2 days after applying the solution and lasted about 3 days. Based on this result, the 0.2% solution was chosen as the dosage to apply to the next cold sore.

Upon the next HSV outbreak that produced a cold sore on the subject's lower lip, the subject applied a 0.2% DNCB solution in acetone to the site of the cold sore on his lower lip and left it on overnight. In the morning he washed it off. A mild erythema in the area of the cold sore developed over 2-3 days and lasted a further 5 days, and the cold sore resolved in about 7 days, which was a typical duration for this individual or a slightly shorter duration than normal. Following this treatment, the subject experienced outbreaks of cold sores on his lower lip approximately weekly for the next 4 weeks, but they were much less severe and of much shorter duration than before. Each outbreak would begin and completely resolve in one day. Approximately two months after the first application of DNCB to his lip, the subject had a mild cold sore and applied the 0.2% DNCB solution in acetone to the site of an HSV lesion on his lower lip as soon as the outbreak began. This time, the inflammation and erythema with the application were more severe than they had been with the first application of DNCB to the lesion on his lip two months previously. We think this may be because the immune system was recognizing not just the DNCB but also the herpes virus antigens with this second application. With the greater inflammation, the cold sore outbreak was worse than any of the outbreaks between the first and second DNCB treatments. Those outbreaks had been very mild, but this HSV outbreak lasted for about 7 days, and was as severe or even slightly more severe than a typical outbreak before the DNCB treatments were undertaken. The outbreak seemed to worsen as the inflammation associated with the DTH response worsened, and only lessened when the DTH response subsided.

Following that second DNCB treatment at the site of a lesion, the subject had no outbreaks at all for 6 months, which he reports as the longest he has ever gone without a cold sore. At the end of this 6-month period, he had a mild cold sore and chose to apply a 0.1% DNCB solution to the cold sore. Again, this induced a moderate DTH response, and the inflammation seemed to worsen the outbreak, so the outbreak lasted about 10 days. When the outbreak subsided, the subject went another 6 months without any outbreaks to the present time.

For several months before and for the entire time described herein after the initial DNCB treatment, the subject took no antiviral medicines.

Example 2

Treatment of Herpes Labialis by Squaric Acid Dibutyl Ester

Thirty patients are recruited meeting the following criteria:

| Inclusion Criteria | Exclusion Criteria |
| --- | --- |
| 18-85 years old | |
| Men and non-pregnant/non-lactating women | Pregnancy or attempting to become pregnant |
| Able to understand and comply with all requirements of protocol | Unable to return for follow-up visits or comply with protocol |
| Six or more episodes of herpes labialis of a recurring nature per year | Prior treatment with Squaric Acid and current active therapy |
| | Cancer treatment and any immunodeficiency |

In a screening interview, vital signs are recorded, and information is collected on any medications the patient is currently taking, previous and current treatments for cold sores, severity and duration of cold sores.

Visit 1:

Upon entering the study, patients are sensitized to squaric acid dibutyl ester (SADBE) by dipping a cotton-tipped swab in a 2% solution of SADBE in DMSO and swabbing a 1 $cm^2$ area on the forearm. Participants are told then to wait at least 2 weeks for their first treatment.

Throughout the study, the participants are asked to maintain a subject diary, in which they record each day any symptoms they experience, including fever, swelling, pain, redness, itching, burning, the size of any lesions, and any medications taken.

Visit 2:

After the 2-week period to allow development of sensitivity to SADBE, upon the beginning of his or her next outbreak (within 72 hours of the first signs of an outbreak), each participant is swabbed at the site of the herpes labialis lesion with a 0.5% solution of SADBE in DMSO.

Visit 3:

Upon the next distinct outbreak at least 2 weeks after the previous treatment at visit 2, study diaries are collected. If the diary reflects redness, blistering, or burning greater than 0.5 cm beyond the clinical lesion with the previous SADBE treatment, the dosage of SADBE is decreased to 0.1%. If the diary reflects no redness or inflammation attributable to SADBE treatment, dosage is increased to 2%. Otherwise, dosage is maintained at 0.5%. Participants are swabbed at the site of the herpes labialis lesion with the SADBE solution.

If the hypersensitivity reaction produced by SADBE is excessive, patients are treated with a topical steroidal anti-inflammatory cream. When a patient requests, outbreaks are treated with oral valacyclovir until the outbreak resolves.

For at least 6 months after visit 2, patients maintain their diaries. Every two months the diaries are collected.

At visit 1, before applying SADBE, a blood sample is collected from each patient for use in a peripheral blood mononuclear cell (PBMC) proliferation assay to test immune response to herpes virus.

Two months after visit 2 (the first treatment application of SADBE to an HSV lesion) if the patient has not experienced a recurrence outbreak after visit 2, or one month after visit 3 (the treatment application of SADBE to a lesion of a second outbreak), a blood sample is collected from the patient. The first, pretreatment, blood sample and the second, posttreatment, blood sample are used to conduct PBMC proliferation assays to test immune response to herpes virus before and after treatment.

PBMC Proliferation Assay

Venous blood is collected in heparinized test tubes for mononuclear cell isolation prior to treatment and after treatment at the times described above. Sample specimens are immediately transferred to the laboratory for processing.

Venous blood (15 ml) is transferred to a 50 ml centrifuge tube, diluted to a total volume of 30 ml with saline or PBS, underlayed with Fico/Lite-LymphoH™ (Atlanta Biologicals) and centrifuged for 20 minutes at 2100 rpm in an Eppendorf Model 5804R centrifuge. Interface cells are collected and washed 2× with saline/PBS, centrifuged and resuspended in saline/PBS. Cell counts are performed using a Beckman Coulter Z1 particle counter and the cells resuspended in freezing media (RPMI/20% human AB serum) and stored at −70° C. Pre- and post-treatment peripheral blood mononuclear cells from each patient are stored for proliferation assays.

KOS HSV-1 virus (American Type Culture Collection) is grown in culture in VERO cells and collected. Virus is filtered through a 45:m filter attached to a 3 ml syringe, into sterile cryovials. The titer of the virus stock is determined. Virus is then heat inactivated, and stored at −20° C. for use to stimulate PMBC in the proliferation assays.

Peripheral blood mononuclear cells are thawed, washed 2× in saline/PBS and resuspended at $5 \times 10^5$ cell/ml in RPMI/10% human AB serum. Cells are plated at 200 μl/well. Heat inactivated KOS HSV-1 particles ($2 \times 10^5$ pfu per well) are added to the experimental wells. Concanavalin A (5:g/ml) is added to other wells as a positive control. Negative control wells have no additions. Plates are incubated at 37° C., 5% $CO_2$ for 5 days and then assayed for proliferation with Cell Counting Kit 8, a tetrazolium dye assay (Dojindo Molecular Technologies, Gaithersburg, Md.).

Results are calculated by averaging optical density of the wells in each of the groups. A stimulation index is calculated to reflect the proliferation in the wells stimulated by killed HSV as compared to the positive and negative controls. The average optical absorbance of the positive controls is set as a stimulation index (SI) value of 100 and the average absorbance of the negative controls as a SI value of 0.

Results:

A total of 46 patients have been enrolled in the study and have not dropped out.

The groups are:

| Group name | Sensitization solution | Treatment solution |
|---|---|---|
| A (Placebo) | 0% SADBE in DMSO | 0% SADBE in DMSO |
| B | 2% SADBE in DMSO | 0.5% SADBE in DMSO |
| C | 2% SADBE in DMSO | 0.2% SADBE in DMSO |

Surprisingly, it was found that persons in the treatment groups B and C receiving 2% SADBE in DMSO as a sensitization dose usually did not have a subsequent outbreak during the study time, whereas those in the placebo group A usually did. This is shown in Table 1.

TABLE 1

Proportion of subjects in each treatment group having a cold sore outbreak within 120 days after receiving the sensitization dose.
Persons having an outbreak within X days after the sensitization dose

| Days | A (Placebo) | B | C | B + C | p value for A proportion versus B + C proportion |
|---|---|---|---|---|---|
| 30 days | 5 (of 15) | 2 (of 16) | 3 (of 15) | 5 (of 31) | 0.26 |
| 45 days | 8 (of 15) | 4 (of 16) | 4 (of 15) | 8 (of 31) | 0.099 |
| 60 days | 9 (of 15) | 5 (of 16) | 4 (of 15) | 9 (of 31) | 0.0583 |
| <120 days | 11 (of 15) | 6 (of 16) | 4 (of 15) | 10 (of 31) | 0.0125* |
| Total persons in group | 15 | 16 | 15 | 31 | |

*statistically significant (p < 0.05)

The p value was calculated using the Fischer's two-tailed exact test.

In addition, the proportion in group A who had a first outbreak between 30 and 120 days after receiving the sensitization dose was 4 of 14, while the proportion in pooled groups B and C was 5 of 26, and this difference is also statistically significant (p<0.05).

The average days to the first outbreak after the sensitization dose was also measured. If a patient had not had an outbreak by 120 days, a value of 120 days was used. The A: placebo, 0% SADBE in DMSO.

TABLE 2

Average days to first outbreak after the sensitization dose (using 120 days if a subject has not had an outbreak in 120 days.)
Days to 1st outbreak

| | A (Placebo) | B | C | B + C |
|---|---|---|---|---|
| Average | 63.0* | 88.5 | 94.7 | 91.5* |
| Standard deviation | 41.80 | 40.86 | 48.4 | 44.02 |
| n | 15 | 16 | 15 | 31 |
| <120 days | 11 (of 15) | 6 (of 16) | 4 (of 15) | 10 (of 31) |
| Total in study | 15 | 16 | 15 | 31 |

*statistically significant difference, p < 0.05, t test.

The difference in average days between group A (placebo) and the pooled groups B and C is statistically significant (p=0.041).

Table 3 shows the days to the first new outbreak from the date of the sensitization dose (2% SADBE or placebo applied to the inner aspect of the upper arm) in each patient.

TABLE 3

Days to first new outbreak after sensitization dose on upper arm

| Placebo group | 2% SADBE |
|---|---|
| 19 | 14 |
| 20 | 14 |
| 24 | 15 |
| 25 | 18 |
| 28 | 34 |
| 40 | 37 |
| 40 | 41 |
| 42 | 50 |
| 56 | 80 |

TABLE 3-continued

Days to first new outbreak after sensitization dose on upper arm

| Placebo group | 2% SADBE |
|---|---|
| 64 | 91 |
| 98 | >120 |
| 107 | >120 |
| >120 | >120 |
| >120 | >120 |
| >120 | >120 |
| | >120 |
| | >120 |
| | >120 |
| | >120 |
| | >120 |
| | >120 |
| | >120 |
| | >120 |
| | >120 |
| | >120 |
| | >120 |
| | >120 |
| | >120 |
| | >120 |
| median = 42 days | median = greater than 120 days |

The median time to the next outbreak in the placebo group was 42 days, while in the treatment group it was greater than 120 days. If the outbreaks occurring in the 21 days after the sensitization dose are excluded, the median time to the next outbreak was 56 days in the placebo group and again over 120 days in the treatment group, counting from the day of the sensitization dose. Counting from day 21 after the sensitization dose, the median time to the next outbreak was 35 days (56 minus 21) for the placebo group and greater than 99 days for the treatment group.

Thus, a single sensitization dose of 2% SADBE in DMSO on the upper arm significantly reduced time to outbreaks and the proportion of persons who had an outbreak at all for at least 120 days. It prevented future outbreaks. This occurred even without a treatment dose applied to the lip during an outbreak.

Many of the subjects had a rash (erythema) from the sensitization dose, which was not expected. In the placebo group A, 2 of 13 had a rash, and in the pooled treatment groups B and C, 17 of 28 had a rash (not all subjects reported whether they had a rash or not, which is why the total number of subjects here differs from Tables 1 and 2).

All patents, patent applications, and other publications cited are incorporated by reference.

What is claimed is:

1. A method of treating herpes simplex virus (HSV) infection comprising:
    an administering step comprising:
        applying a topical immunosensitizer to the skin of a person infected with HSV at a time when the person is not having an HSV outbreak, or applying a topical immunosensitizer to the skin of a person infected with HSV during an HSV outbreak wherein the applying is at a site other than a site of an HSV lesion;
    wherein the method does not further comprise (i) applying a topical immunosensitizer to the skin of a person infected with HSV on an HSV lesion at a time of an HSV outbreak in the person; or (ii) intradermally injecting a recall antigen into a person infected with HSV in an HSV lesion at the time of an HSV outbreak in the person;
    wherein the method reduces the frequency of HSV outbreaks in the person after the administering step;
    wherein the person has had HSV outbreaks before the administering step and is in recognized need of treatment for HSV infection;
    wherein the administering step comprises applying the topical immunosensitizer to skin on the forearm or on the inner aspect of the upper arm of the person;
    wherein the topical immunosensitizer comprises squaric acid dibutyl ester (SADBE); and
    wherein the person has herpes labialis.

2. The method of claim 1 wherein the administering step comprises applying the topical immunosensitizer to skin on the inner aspect of the upper arm of the person.

3. The method of claim 1 wherein the topical immunosensitizer is applied as a solution in DMSO.

4. The method of claim 1 wherein the HSV is HSV-1.

5. The method of claim 1 wherein the HSV is HSV-2.

6. The method of claim 1 wherein the method increases time between outbreaks by at least 2-fold.

7. The method of claim 1 wherein the method increases stimulation index of peripheral blood mononuclear cells (PBMC) from a patient in a proliferation test with stimulation of proliferation by killed HSV particles as compared to the stimulation index of PBMC from the patient before treatment.

8. The method of claim 1 wherein the method increases median time to the next outbreak after the administering step by at least 2-fold.

9. The method of claim 1 wherein the method increases median time from day 21 following the administering step to the next outbreak that begins at least 21 days after the administering step by at least 2-fold.

10. The method of claim 1 wherein the method further comprises a second administering step comprising:
    (a) applying a topical immunosensitizer to the skin of a person infected with HSV at a time when the person is not having an HSV outbreak, or applying a topical immunosensitizer to the skin of a person infected with HSV during an HSV outbreak wherein the applying is at a site other than a site of an HSV lesion.

11. The method of claim 10 wherein the second administering step occurs 7 days to 30 days after the first administering step.

12. The method of claim 10 wherein the second administering step occurs 7 days to 365 days after the first administering step and occurs at a time when the person is having an HSV outbreak.

* * * * *